US006855802B1

(12) United States Patent
Triebel et al.

(10) Patent No.: US 6,855,802 B1
(45) Date of Patent: Feb. 15, 2005

(54) MUTATED PEPTIDE COMPOUNDS, DERIVED FROM HSP70, USEFUL IN CANCER IMMUNOTHERAPY

(75) Inventors: Frédéric Triebel, Versailles (FR); Catherine Gaudin, Savigny-sur-Orge (FR)

(73) Assignee: Institut Gustave Roussy, Villejuif (FR)

( * ) Notice: Subject to any disclaimer, the term of this patent is extended or adjusted under 35 U.S.C. 154(b) by 0 days.

(21) Appl. No.: 09/673,795

(22) PCT Filed: Apr. 22, 1999

(86) PCT No.: PCT/FR99/00957

§ 371 (c)(1),
(2), (4) Date: Oct. 20, 2000

(87) PCT Pub. No.: WO99/54464

PCT Pub. Date: Oct. 28, 1999

(30) Foreign Application Priority Data

Apr. 22, 1998 (FR) ............................................ 98 05033

(51) Int. Cl.$^7$ .......................... A61K 38/00; A01N 37/18
(52) U.S. Cl. .......................................... 530/300; 514/2
(58) Field of Search ............................... 530/300, 323, 530/328, 333; 514/2, 21, 44

(56) References Cited

FOREIGN PATENT DOCUMENTS

WO          WO9002564 A     *   3/1990

OTHER PUBLICATIONS

Freshney (Culture of Animal Cells, A Method of Basic Technique, Alan R. Liss, Inc., 1983, New York, p4).*
Dermer (Bio/Technology, 1994, 12:320).*
Crystal, R.G. (Science, vol. 270, Oct. 1995, pp. 404–410).*
Tait et al. (Clin.Canc.Res., vol. 5, Jul. 1999, pp. 1708–1714).*
Gura (Science, v278, 1997, pp. 1041–1042).*
Gaiger et al (Blood Aug. 15, 2000;96(4):1480–1489).*
Prakken et al (PNAS USA Apr. 1997; 94:3284–3289).*
Costa MH et al (Appl Biochem Biotechnol Apr. 1998; 73(1):19–28).*
International Search Report for PCT/FR99/00957.
Fagan et al., Sequence and characterization of two HSP70 genes in the colonial protochordate *Botryllus schlosseri; Immunogenics* (1996) 44:134–142.
Gutierrez et al., Chemical modifications of a recombinant bovine stress–inducible 70 kDa heat–shock protein (HSP70) mimics HSP70 isoforms from tissues; *Biochem. J.* (1995) 305:197–203.
Borchiellini et al., Phylogenetic analysis of the HSP70 sequences reveals the monophyly of metazoa specific phylogenentic relationships between animals and fungi; *Mol. Biol. Evol.* (1998) 15:647–655.
Sainis et al., The hsc70 gene which is slightly induced by heat is the main virus inducible member of the hsp70 gene family; *FEBS Letters* (1994) 355:282–286.
Gaugler et al., A new gene coding for an antigen recognized by autologous cytolytic T lymphocytes on a human renal carcinoma; *Immunogenetics* (1996) 44:323–330.
Blachere et al., Heat shock protein–peptide complexes, reconstituted in vitro, elicit peptide–specific cytotoxic T lymphocyte response and tumor immunity; *J. Exp. Med.* (1997) 186:1315–1322.
Rosenberg et al., Immunologic and therapeutic evaluation of a synthetic peptide vaccine for the treatment of patients with metastatic melanoma; *Nature Medicine* (1998) 4:321–327.

* cited by examiner

*Primary Examiner*—G. Nickol
*Assistant Examiner*—C Yaen
(74) *Attorney, Agent, or Firm*—Young & Thompson

(57) ABSTRACT

The invention concerns a method for identifying peptide compounds derived from hsp70, having at least one mutation relative to the hsp70 natural sequence, said compounds bringing about a response T specific of tumours, and the peptide compounds obtainable by said method. The invention also concerns the use of said peptide compounds for performing repeated immunization in a subject so as to interrupt immune tolerance for the corresponding natural (non-mutated) peptide. Said peptide compounds are useful for preparing a medicine designed in particular for treating cancer optionally in combination with any agent provoking tumour cell stress.

8 Claims, 9 Drawing Sheets

Figure 1:
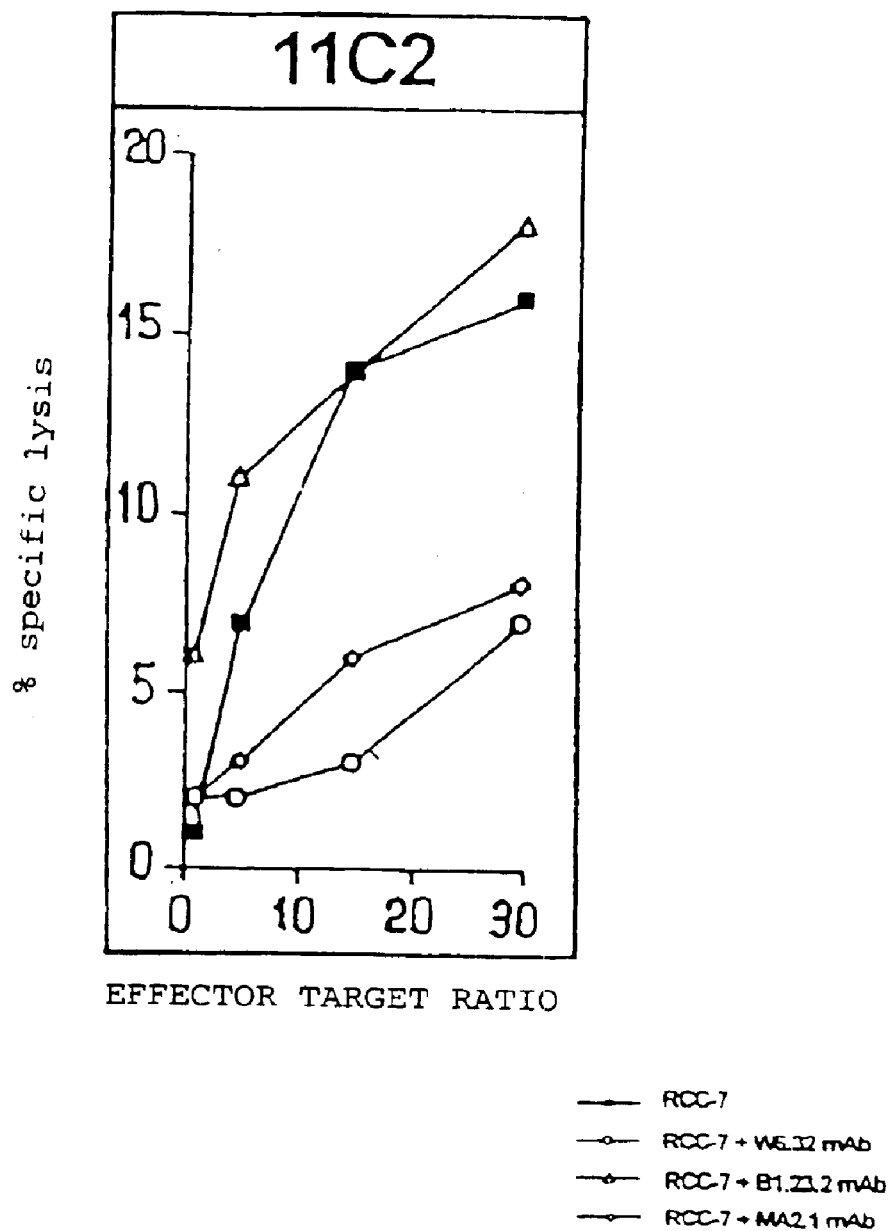

Specific lytic activity of clone 11C2
against the RCC-7 autologous cell line

Secretion of TNF by the 11C2-CTL clone during stimulation with the RCC-7 autologous cell line Cytotoxicity of the 11C2 CTLs on multiple RCC allogenic cell lines Stimulation of the 11C2 CTL by the cells transiently cotransfected with the autologous HLA-A*0201 cDNA and the A18 cDNA Location of the epitope region of HSP70 recognized by the 11C2 CTL Lysis by 11C2 CTL of the autologous cell line transformed with EBV and incubated with the peptides encoded by HSP70-2

Induction of HLA-A2 expression on T2 cells by the HSP70-2 antigenic peptides

Northern Blot Analysis

MUTATED PEPTIDE COMPOUNDS, DERIVED FROM HSP70, USEFUL IN CANCER IMMUNOTHERAPY

The present invention relates to a method for identifying peptide compounds derived from hsp70 which have at least one mutation or one modification with respect to the natural hsp70 sequence, said compounds bringing about a T response specific for tumors, and to the peptide compounds which can be obtained with said method. The invention also relates to the use of these peptide compounds for performing repeated immunization in an individual so as to break down immune tolerance for the corresponding natural peptide (nonmutated). The peptide compounds are useful for manufacturing a medicinal product intended in particular for treating cancer, optionally in combination with any agent which causes tumor cell stress.

For a long time, researchers have attempted to find mechanisms for stimulating the immune rejection of tumors, starting from the hypothesis that antigens, which can be used as targets, are expressed at the surface of the cancerous cells. The delicate balance between tumor growth and regression has been the subject of multiple theories, in particular with regard to the role of the immune system. Immunosurveillance is an attractive theory according to which tumors are destroyed at the very first stage of their development by immune defense mechanisms. For example, the observation that many tumors are infiltrated by lymphoid cells appears to be a sign of favorable prognostic.

However, the incidence of cancers in immuno-deficient individuals is not significantly higher than in the general population. This fact has been correlated by experiments carried out on of deficient mice (nude mice). Specifically, these mice bred under sterile conditions, develop no more tumors than the mice with a wild-type genotype. Thus, it is commonly accepted today that the very slightly increased risk of the appearance of cancers in immuno-deficient individuals is directly correlated with the incidence of viral infections (oncogenic viruses). This suggests that the immune response would intervene by limiting virus dissemination and by recognizing the cancerous cells carrying viral antigens. When an oncogenic virus integrates the genome of the host cell, there is expression by said cells of modified proteins which are capable of constituting antigenic targets.

However, with regard to tumors of nonviral origin, the major problem for the immune defenses comes from the fact that there are no flagrant antigenic differences with normal cells. This is why these tumors are thought to escape, to a certain degree, immuno-surveillance. Some antigens specifically expressed by nonviral tumors have been demonstrated. For example, the CALLA protein (Common Acute Lymphoblastic Leukemia Antigen), which is normally expressed in hematopoietic cells and repressed in normal mature B lymphocytes, is overexpressed in lymphoblasts. Thus, antigenic proteins of tumors are not foreign to the organism and are naturally present in some normal cells.

Thus, the thing which distinguishes antigenic proteins, and which can be recognized by the immune defenses, is a mutation, a modification (for example a posttranslational modification of an amino acid) or a differential distribution, or alternatively an over-expression. It is clear that the recognition of said proteins by lymphocytes is reduced because of their intrinsic presence in normal cells (negative clonal selection). Persons skilled in the art must therefore resolve this problem in order to find an effective mechanism for activating the immune defenses with respect to cancerous cells. The challenge is all the greater given that the concentration of the antigens is low and that their presentation by MHC molecules is sometimes inadequate.

The object is thus to identify antigenic peptides specific for tumors, which should be capable, of effectively stimulating the immune defenses in vivo, in particular cytotoxic T lymphocytes. These peptides can be used as vaccines optionally comprising costimulators such as cytokines or lymphokines.

Farace et al, (1997), has demonstrated that the induction of the inflammatory response in delayed-type hypersensitivity and at the site of the vaccine in an immunized patient, originates from the recruitment of only a few T-cell clones. These cells correspond to the lymphocytes which have infiltrated into a tumor and have already been amplified, before immunization. Thus, tumor antigens can be used to locally recruit and amplify T lymphocytes specific for tumors. The cells activated in vivo can be further amplified by administering IL-2. Specifically, Kumar A. et al (1996) has shown that T-cell clone activity is induced in the blood, and in the tumors, of patients receiving IL-2.

It has been difficult to isolate and to amplify the clones of cytotoxic T lymphocytes (CTLs) specific for renal carcinoma cells, Bernhard et al, (1994) and Brouwenstijn et al, (1996). This difficulty originates from the lack of proliferation of the tumor-infiltrating lymphocytes (TILs), particularly in cells of renal carcinoma (RCC), Alexander et al, (1993). However, some results indicate that RCCs might be immunogenic in vitro since these tumors are often greatly infiltrated by T lymphocytes, in particular by TCR $\alpha/\beta^+$ DR$^+$ Th1-polarized lymphocytes, Angevin et al, (1997), and because of the relatively high level of response (15 to 20%) to certain immunotherapy protocols, Rosenberg et al, (1992).

An antigen, which is recognized by RCC autologous CTLs, has been identified by Gaugler et al, (1996). This antigen is encoded by a gene, termed RAGE 1, which is expressed in many tumors but which is absent from normal adult tissues, except those of the retina. It is clear that the use of RAGE 1 for cancer immunotherapy presents problems since this might generate reactions of autoimmune rejection of the retina. Preparations comprising the combination hsp-peptide isolated from cancerous cells or from cells infected with viruses confer immune protection with respect to the tumors and to the infected cells, Blachere et al, (1997). Other documents, such as WO 97/10001, WO 97/06828, WO 97/26910 or Tamura et al, (1993) and (1997), relate to the treatment of neoplastic cells with hsp70/cancerous cell-derived peptides complexes. These documents of the prior art disclose the capacity of hsp70 to absorb like a sponge the peptides from cells. The isolation of hsp70 originating from cancerous cells makes it possible to identify multiple protein fragments of tumors, which may potentially be antigenic. It has now been found that mutations or modifications in the hsp70 protein exist which are expressed in tumors, and that such mutations or modifications prove to be immunogenic. Since it is known that hsp70 may be overexpressed in tumors, said peptides are useful for inducing a breakdown of tolerance against hsp70.

Thus, no document of the prior art discloses or suggests the present invention as defined below.

DESCRIPTION OF THE INVENTION

The present invention relates to a method for identifying peptide compounds derived from hsp70 which have at least one mutation or one modification with respect to the natural hsp70 sequence, said compounds bringing about a T response specific for tumors, comprising the following steps:

a) PCR-amplifying a DNA fragment encoding hsp70, obtained from one or more tumor(s),
b) cloning the DNA obtained in step a) into a vector capable of replicating in a bacterium,
c) sequencing said fragment in each bacterial colony obtained after culturing the bacteria of step b), and identifying the mutation(s) in hsp70,
d) determining the immunogenicity of the mutated peptide fragments among those identified in step c). Advantageously, step d) consists of an Elispot assay. It is possible to simply test the immunogenicity of the peptide fragments which have an anchoring sequence for a given HLA molecule (see below, "reverse immunology" method).

The peptide fragments to be tested in step d) can easily be obtained by chemical synthesis using general knowledge in the technical field.

In the context of the invention, the term "hsp70" is intended to mean both hsp70-1 and hsp70-2. The Elispot assay is widely described in the documents of the prior art. For example, Herr et al, (1998) relates to an Elispot method for detecting and quantifying CD8+T lymphocytes secreting TNF-α. In summary, MultiScreen-HA plates (Milllipore, Bedford, Mass.) are coated with an anti-TNF-α antibody (clone 195; Boehringer Mannheim), and CD8+T lymphocytes are added E2 in the presence of antigenic peptides. The secreted TNF-α is detected with a rabbit anti-TNF-α antibody (Serotec, Oxford, UK), a biotin-coupled rabbit anti-IgG antibody (Boehringer Mannheim) and the biotin-avidin-peroxidase complex (Vector, Burlingame, Calif.). The number and surface area of the zones in which the cytokine is present are determined automatically by computer (Herr et al, (1997). Other documents, such as Herr et al, (1996) materials and methods section, paragraph 2, pages 132 to 135, and Scheibenbogen et al, (1997) page 933, disclose this method, and are also incorporated into the description by way of reference.

The invention also relates to a method for revealing artificial point mutations or modifications which can increase the immunogenicity of the mutated peptide compounds derived from hsp70, wherein it comprises the following steps:
a) determining fragments which have a sequence of approximately 9 to 10 amino acids comprising an anchoring motif for a given HLA molecule,
b) introducing an additional point mutation or modification at residues 4, 5, 6, 7 or 8,
c) determining the immunogenicity of the peptide fragments obtained in step b).

Preferably, step c) consists of an Elispot assay. This method is well known to persons skilled in the art. There may also be incorporated, by way of reference, into the description, the teachings which are to be found at the following Internet address:
www.bimas.dcrt.nih.gov/molbio/hla_bind/
This method makes it possible to determine any artificial point mutation or modification, (not present in human tumors) which would be capable of improving the active principle (the immunogenic mutated peptide), using the so-called "reverse immunology" method. Based on the knowledge of the amino acid sequence of a protein, such as hsp70, it is possible to predict which of the peptides can bind to an HLA pocket, whatever its specificity (HLA-A2, HLA-A1, HLA-B7, etc.), then to test these peptides in vitro for their capacity to bind effectively to the HLA allele under consideration, and then to introduce a point mutation or modification into the amino acids at certain positions which are critical for affinity. The BIMAS computer program enables such a prediction to be obtained. The general rules regarding the amino acids involved in anchoring to HLA molecules are given in Parker et al, (1992 and 1994) and Rammensee et al, (1995). This information is incorporated by way of reference into the description. Of course, the method according to the invention is not limited to the use of the BIMAS program, and can be used with any equivalent program.

Another aspect of the invention relates to a peptide compound which can be obtained using a method described above. This compound is characterized by the fact that it comprises a sequence of at least 8 consecutive amino acids of hsp70, by the fact that it has at least one mutation or one modification with respect to the natural hsp70 sequence, and by the fact that it brings about a specific T response. A specific aspect relates to a peptide compound having at least 80% homology with the amino acids between positions 286 and 294 of hsp70.

Preferably, the amino acid at position 293 is W isoleucine, leucine, valine, alanine, glycine or phenylalanine, more particularly isoleucine. The preferred peptide compounds of the invention have at least one of the following sequences:

| SEQ ID No. 1: | $_{286}$-SLFEGIDIY$_{294}$ |
| SEQ ID No. 2: | $_{286}$-SLFEGIDIYt$_{295}$ |

Said compounds can also comprise unnatural amino acids which may or may not be equivalent to the natural amino acids.

The term "peptide compound" is intended to mean an entity consisting at a minimum of a peptide fragment of hsp70 as defined above, or of a series of said peptide fragments, and having optionally one or more other elements other than natural or unnatural amino acids. The purpose of these elements is to chemically or physically protect said peptide fragments, and/or to promote their absorption by the body, and/or their administration, and/or their bioavailability. For example, this protection enables the peptides to reach their targets without undergoing the action of diverse proteases present in the body. Such chemical modifications may also increase the affinity of an antigenic peptide for HLA-A2 molecules, and allow an increased effectiveness of the vaccine in vivo to be obtained, Rosenberg et al, (1998).

Said elements can be, for example:
  Protective chemical groups known to persons skilled in the art, which react with the NH2 and/or COOH ends of a peptide, this modification not significantly lowering the immunogenic nature of the peptide.
  Chemical groups which improve the effectiveness of the vaccine in vivo.
  The lipids or fatty acids which are covalently bonded to the peptide fragments so as to form peptide compounds termed lipopeptides. Palmitic acid is one example among others, Vitiello et al, (1995), which is incorporated into the description by way of reference.
  A carrier protein for said peptide fragments which possesses restriction sites and enables the intact peptide fragments to be conveyed to their sites of action in the body.

A second aspect of the invention relates to the DNA fragments encoding the peptide fragments mentioned above. The term "DNA fragments" is intended to mean single-stranded or double-stranded DNA, cDNA and/or RNA fragments. The nucleotide sequence corresponding to the amino acid sequence of said peptide fragments can vary so as to comprise all the various possible codons for a given amino acid according to the principle of degeneracy of the genetic code. A subject of the present invention is also a vector for expressing a peptide fragment, containing an abovementioned DNA fragment fused to a promoter which is strong and effective in eukaryotic and/or in prokaryotic cells, in particular in human cells. The vector can be viral, a plasmid vector or a pseudovector, and can comprise selection markers and express immunological adjuvants such as cytokines and/or lymphokines.

The invention also relates to dendritic cells loaded with peptide compounds, and dentritic cells transformed with the expression vector expressing the peptide fragments. These cells can also be macrophages. Nestle et al, (1998), discloses a vaccination method which consists in loading the dendritic cells taken from a patient with antigenic peptides (in culture in vitro), and injecting them into the lymphatic system of this same patient. This publication is incorporated into the description by way of reference.

The subject of another aspect of the invention is a pharmaceutical composition comprising a peptide compound, or a mixture of peptide compounds, according to the invention and a pharmaceutically acceptable vehicle. This composition can also comprise one or more immunological adjuvants, in particular factors which are cytotoxic for tumors.

The invention also relates to a pharmaceutical composition comprising an expression vector as mentioned above and a pharmaceutically acceptable vehicle, or a DNA fragment according to the invention, or alternatively the cells indicated above, and a pharmaceutically acceptable vehicle.

A further aspect of the invention relates to a combination product comprising at least one peptide compound as claimed in the invention and at least one agent which induces cellular stress, for simultaneous or separate use, or for use spread out over time, intended for treating cancer. Preferably, said agent can be capable of inducing overexpression of heat shock proteins, in particular hsp70. Advantageously, this agent is an apoptosis inducer, selected in particular from DNA-damaging agents and glucocorticoid receptor ligands, or from pro-apoptotic second messengers. The combination product can comprise a viral vector which has a gene which encodes an enzyme for activating said pro-apoptotic agents, in particular thymidine kinase.

The expression "agent which induces cellular stress" refers to any agent which is capable of inducing overexpression of heat shock proteins, in particular hsp70. These agents can be in particular apoptosis-inducers. The expression "apoptosis-inducing agent" is intended to mean any substance which directly or indirectly affects the viability of a cell.

Said apoptosis-inducing agent of the present invention can be selected in particular from DNA-damaging agents and glucocorticoid receptor ligands, or from pro-apoptotic second messengers. These agents can be selected preferably from those commonly used in the treatment of cancer. Thus, said pro-apoptotic second messenger is in particular selected from the following compounds:

glucocorticoid derivatives,
from alkylating agents such as nitrogen mustards, for example cyclophosphamide,
platinum complexes, for example cisplatin,
ethyleneimine derivatives, dimethanesulfonoxy-alkane derivatives,
piperazine derivatives,
from topoisomerase inhibitors, such as topoisomerase 2 inhibitors, for example anthracyclines, epipodophyllotoxin such as etoposide, or topoisomerase-1 inhibitors, for example camptothecin derivatives,
from antimetabolites, such as antifolates, for example methotrexate, antipurines, for example 6-mercaptopurine, or antipyrimidines, for example 5-fluorouracil,
from antimitotic agents, such as vinca alcaloids or taxoids such as taxotere,
and from diverse cytolytic agents such as bleomycin, dacarbazine, hydroxycarbamide, asparaginase, mitoguazone or plicamycin.

These antineoplastic agents are described in Actualité Pharmaceutiques No. 302 (October 1992) pages 38 to 39 and 41 to 43, incorporated into the description by way of reference.

Said apoptosis-inducing agent can also be chosen from gamma radiation used in radiotherapy, etoposide, doxorubicin, dexamethasone, ceramide, such as C8-ceramide, and lonidamine. Some of said anticancer agents are more particularly disclosed in U.S. Pat. No. 5,260,327, which relates to the use of lonidamine for treating metastases, in JO 5017353, which relates to the use of lonidamine in combination with other anticancer agents, and in EP 291151, which discloses the use of phlorizin derivatives. These documents are incorporated into the description by way of reference.

The product according to the present invention can also comprise a viral vector which has a gene which encodes an enzyme which makes it possible to activate the abovementioned compounds and/or agents, for example thymidine kinase. Many patents relate to the use of suicide genes which are activated in specific tissues, in particular for sensitizing cancerous cells to nucleotide analogs. Among these documents, which are incorporated into the description by way of reference, are: EP 494776, EP 690129, EP 657540 and EP 657541, which relate in particular to the manufacturing of a medicinal product comprising a vector which has a gene which is capable of catalyzing the changing of a prodrug into an active substance. More particularly, the subject of EP 657539 is the use of the thymidine kinase gene with a cellular specificity, for treating cancer.

In another embodiment, the agent which induces cellular stress is selected from compounds which induce tumor hypoxia, in particular from angiogenesis inhibitors. Mention may be made in particular of endostatin and angiostatin disclosed by J. Folkman, thrombospondin-1 and -2 (TSP-1, -2) Locopo et al (1998); the factors IFN gamma, TNF alpha and IL-1alpha, Maier et al (1999), and U-995, an inhibitor derived from shark cartilage, Sheu et al (1998). These publications, the review on natural inhibitors, Paper et al (1998), and the general review on the various known inhibitors, Harris et al (1998), are incorporated by way of reference into the description.

The pharmaceutical composition or combination product according to the invention can also comprise one or more immunological adjuvants, in particular agents which are cytotoxic for tumors. These products can comprise a pharmaceutical vehicle which is compatible with IV, subcutaneous, oral or nasal administration, and which is preferably selected from positively or negatively charged liposomes, nanoparticles or lipid emulsions.

The present invention also relates to the use of a peptide compound for manufacturing a medicinal product, in particular intended for treating cancer, particularly solid tumors, especially carcinomas, melanomas, neuroblastomas and neck and head cancers, preferably renal carcinomas.

This medicinal product can be intended for immunization ex situ or in situ. The invention also relates to the use of said peptide compound for increasing, in culture medium, the tumor CTL population and/or inducing the secretion by said CTLs of cytotoxic factors, such as for example IL-2, IFN-γ or TNF, and/or for stimulating the immune defenses, in particular so as to increase the tumor CTL population and/or induce the secretion by said CTLs of cytotoxic factors, such as for example IL-2, IFN-γ or TNF.

Of course, the compositions and products of the invention can be used in combination with radiotherapy. Advantageously, the compositions and products of the invention can be taken advantage of to perform repeated immunization for the purpose of causing a breakdown of tolerance against the corresponding natural peptide (nonmutated) in a patient. Specifically, since it is known that hsp70 is or may be overexpressed in tumors, it is most advantageous to be able to immunize patients against this protein. Immunization with the mutated peptides of this protein is capable of breaking down the tolerance of the immune system of patients with respect to hsp70 and consequently, of specifically stimulating cytotoxic and helper T lymphocytes against cancerous cells, whatever the type of cancer or of patient.

An additional aspect of the invention relates to a method for producing an antibody which binds to an hsp70 mutant, in particular to the hsp70-2 I-293 mutant, comprising the steps consisting in:
a) immunizing a mammal with a peptide compound as claimed in the invention,
b) isolating a monoclonal antibody which binds to hsp70-2-293, particularly to hsp70-2 I-293, in an immunological assay. The present invention also comprises a monoclonal antibody which binds to hsp70-2-293, particularly to hsp70-2 I-293, and a method for detecting the hsp70-2-293 mutation or modification, in particular the hsp70-2 I-293 mutation or modification, in which the steps consist in:
a) bringing a sample taken from an individual into contact with one said monoclonal antibody,
b) allowing the formation of the antibody/hsp70-2-293 complex,
c) detecting hsp70-2-293 by means of a detectable label which is in the complex or which binds to the complex.

In a further embodiment, the present invention relates to a diagnostic kit comprising in particular one or more of said antibodies. This kit can in particular be used for detecting cancer and for the prognostic of established cancer in an individual. Finally, a subject of the invention is also a pharmaceutical composition comprising one or more of said monocolonal antibodies and a pharmaceutically acceptable vehicle. The present invention relates, in the same way, to the use of the abovementioned pharmaceutical composition in medicine, for manufacturing a medicinal product, in particular for treating cancer, particularly for treating solid tumors, advantageously carcinomas, melanomas, neuroblastomas, and neck and head cancers, preferably renal carcinomas.

DETAILED DESCRIPTION OF THE INVENTION

The subject of the present invention thus makes it possible to stimulate the immune defenses by increasing the population of CTLs specific for tumors, and by inducing the secretion by said CTLs of cytotoxic factors. Such an amplification of the specific CTLs amounts to bringing about and to expanding a veritable army of cells which destroy tumors.

Specifically, cytotoxic T lymphocytes play a specific role in antigen recognition, and infiltrate into even solid tumors. The activity of CTLs consists in recognizing the antigen combined with syngeneic class I MHC molecules. The CTLs and the target cell then form a bond via the CD8-TCR association with MHC I.

The steps of the cytotoxicity mechanism are as follows:
Recognition, highly specific binding, and formation of the TCR-CD8-MHCI (antigenic peptide) ternary complex.
Secretion by CTLs of perforin and of various enzymes toward the target cell membrane.
Formation of channels in the target cell membrane by polymerization of the perforin by an enzyme, in the presence of calcium (polyperforin channels).
Passage of proteases and of toxins through the channels, and action inside the target cell.
Other toxic factors, such as TNF-α, lymphotoxin (TNF-β) and IFN-γ, released by the CTLs bind to specific receptors of the target cell membrane. Apoptosis is then observed, characterized by the fragmentation of DNA, by budding of the cytoplasmic membrane, and by the disintegration of the cell into small fragments (apoptotic bodies).

A subject of the invention is thus to supply the body with sufficient amounts of peptides which have a high immunogenic potential and are specific for tumors. Such peptide fragments are very rare, diluted among an infinite number of peptides, and difficult to identify. In fact, the binding of the peptides with the MHC molecule is located in an invagination which has a specific topology and specific physico-chemical properties, which vary depending on the nature of the amino acids involved. Thus, a peptide (approximately 9 amino acids) binds to an MHC as a function of the nature of these side chains and of its complementarity with the MHC molecule cavity. This association with the MHC takes place in specific intracellular organisms. Antigenic proteins are generally degraded to peptides in proteasomes (ubiquitous multicatalytic proteinase complexes) before the transport of said peptides into the rough endoplasmic reticulum (RER). The MHC I synthesis and the assembly with the peptides takes place in the RER. Then, the antigen-MHC I complexes are exported to the surface of the cells via the Golgi apparatus. It is thus understood why only certain peptides can bind to the MHC I. With regard to the peptides of the present invention, it has been demonstrated (see below) that they have a very low dissociation constant Kd (very strong association). In this respect, they make it possible to activate the immune system effectively, in particular the CTLs.

The CTLs specific for RCC can be isolated from the tumor-infiltrating lymphocytes (TILs) of a patient. At least 80% of the RCC TILs are activated $DR^+$ $LAG-3^+$ $CD8^+$ cells, Angevin et al. (1997). Subsequent to a short activation of these TILs in vitro, a response of Th1-polarized type was observed (secretion of IL-2 and of interferon γ, but not of IL-4). On the other hand, Finke et al, (1993) has published that the apparent lack of activity of TILs in vivo is due to the poor functioning of the various regulatory cascades in these cells. However, among the 5 CTLs described in the present invention, clone 2A11 (TCRBV1J1S6) is particularly advantageous since it is amplified at the tumor site and represents up to 3% of the TCR $\alpha/\beta^+$ TILs. In addition, this clone recognizes an antigen specific for tumors which is presented by HLA-Cw16, Angevin et al. (1997). This thus demonstrates that the HLA-C molecules are capable of presenting elements at the tumor site in this patient.

hsp70 is encoded by the duplicated locus (hsp70-1, hsp70-2) located in the MHC region at 92 Kb from the C2 gene in the direction of the telomer, Milner et al, (1990). This DNA segment is termed class IV region, and comprises at least 7 genes involved in inflammatory responses and stress responses, Gruen, (1997). The two intron-lacking genes (hsp70-1 and hsp70-2) encode an identical protein of 641 amino acids. There are a few sequence differences in the promoter region and complete divergence in the untranslated 3' region. Using a probe specific for hsp70-2, a rise in the amount of mRNA (2.4 Kb) has been shown subsequent to a heat shock. The hsp70-2 probe has made it possible to detect a small amount of 2.4-Kb mRNA in the constitutive RNA of the cell lines of the RCC tumor and in frozen surgical samples of said tumor. The reason for which the allogenic cell line HLA-A2$^+$ RCC, which expresses low levels of hsp70-2 mRNA, was not killed by CTL 11C2, may be due to the difference observed in target sensitization assays between the mutated peptides and the wild-type decapeptide 286–295 ($5\times10^{-11}$ M and $5\times10^{-8}$ M, respectively, for maximum half-lysis). The transcription and overexpression of wild-type hsp70-2 in COS-7 cells induce the secretion of TNF by CTL 11C2.

It is known that hsps are nonpolymorphic molecules which do not differ in their primary structure among normal tissues and cancers, or among normal cells and cells infected with viruses. Thus, the immunization capacity of preparations comprising hsp is due to the association of the hsp molecules with peptides generated by the cells from which the hsps were isolated. Specifically, the hsp-peptide complexes can be generated in vitro, and the biological activity of such complexes is comparable to that of the hsp-peptide complexes generated in vivo, Blachere et al, (1997). While this observation demonstrates that hsps are adjuvants which elicit a response from CD8$^+$ T cells, our results indicate that certain peptide fragments of hsp70 are directly immunogenic.

For the remainder of the description and for the examples, reference will be made to the figures whose legend is given below.

LEGENDS

FIG. 1: Specific lytic activity of clone 11C2 against the RCC-7 autologous cell line.

The cytotoxicity of the 11C2-CTLs with respect to the RCC-7 cell line was assayed by the standard chromium release assay at various effector/target ratios (E/T ratio). The inhibition of the cytotoxic activity of 11C2 was assayed after several preincubations of the CTLs for two hours with the anti-HLA class 1 mAb (monoclonal antibody) indicated, at a predetermined saturation concentration.

Figure 2:
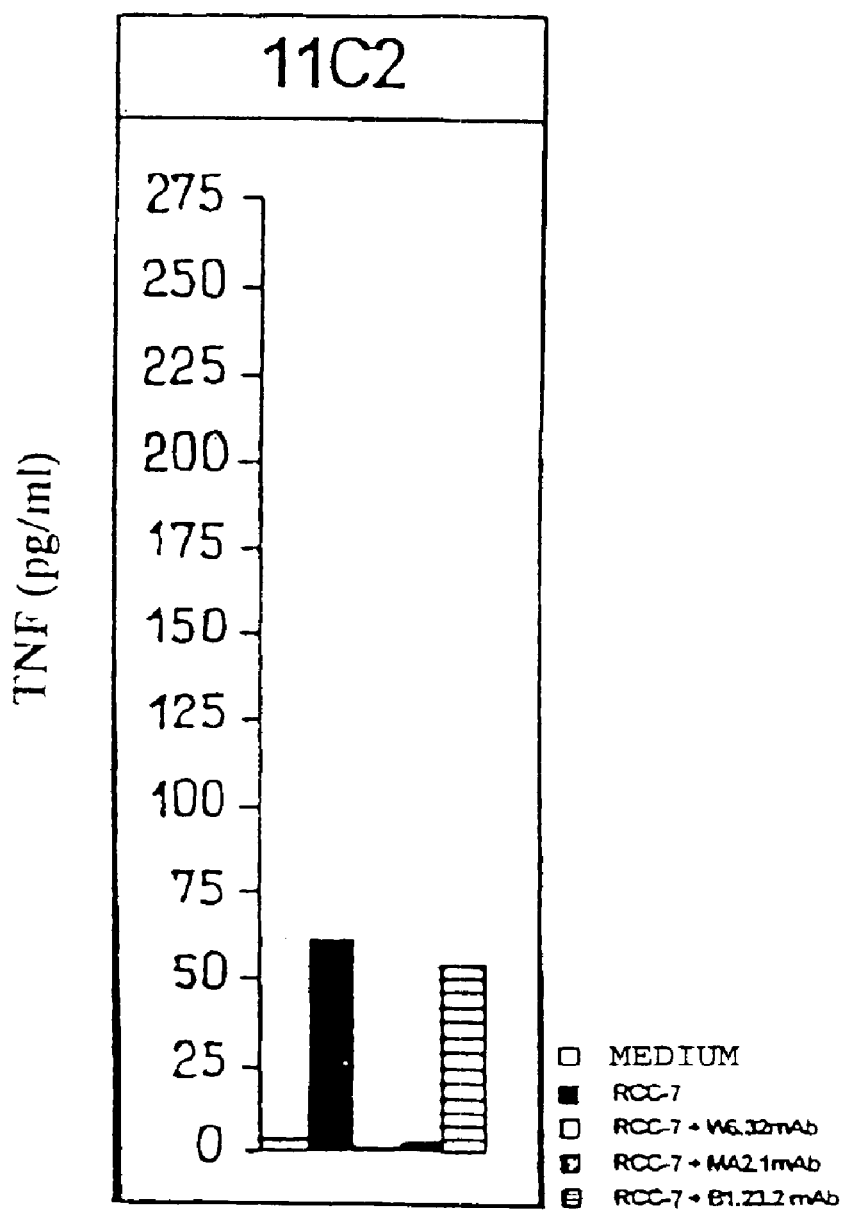

FIG. 2: Secretion of TNF by the 11C2-CTL clone during stimulation with the RCC-7 autologous cell line.

5000 CTLs were incubated with 20,000 RCC-7 cells. The amount of TNF was measured after culturing for 20 hours, by assaying the toxicity of the supernatants with TNF-sensitive WEHI-164 cells (clone 13). The inhibition of the secretion of TNF was assayed after preincubation of clone 11C2 for two hours with the anti-class 1 HLA mAb as indicated.

Figure 3:
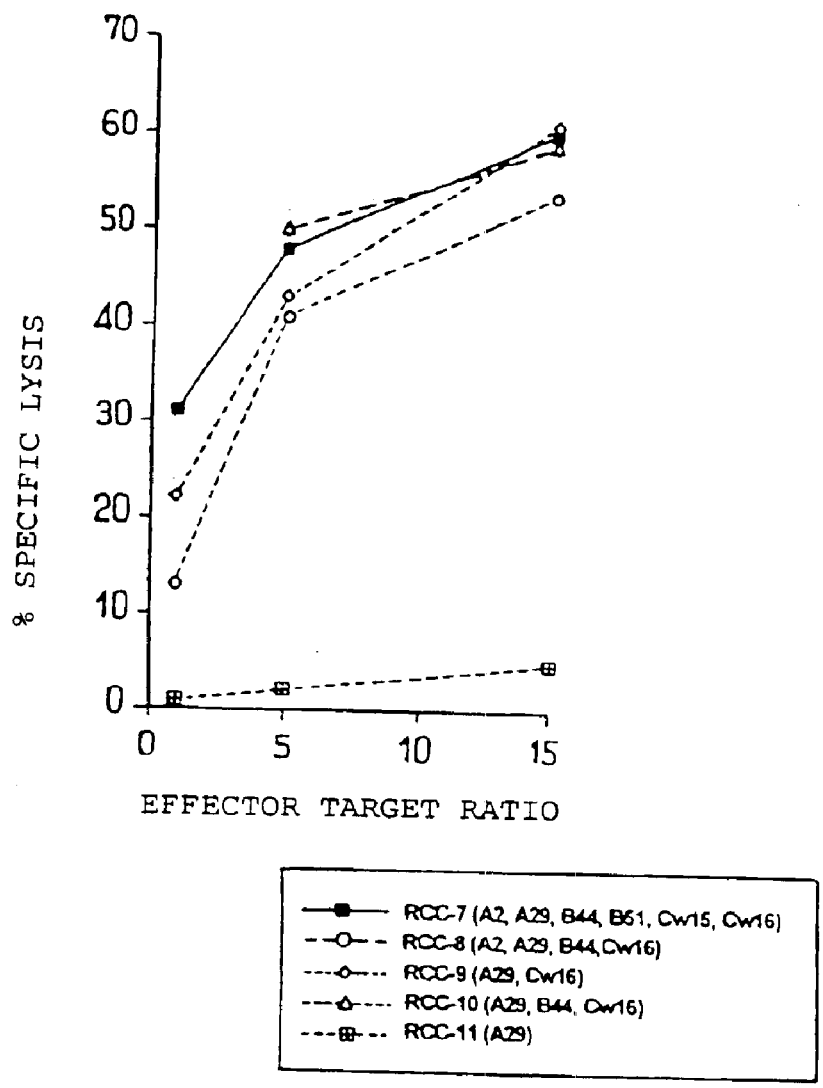

FIG. 3: Cytotoxicity of the 11C2 CTLs on multiple RCC allogenic cell lines.

11C2 was assayed on the RCC-7 autologous line and on multiple RCC allogenic cell lines (RCC-8, RCC-9, RCC-10 and RCC-11) in a standard chromium release assay at the E/T ratio indicated. The HLA molecules shared with RCC-7 are indicated in brackets.

Figure 4:
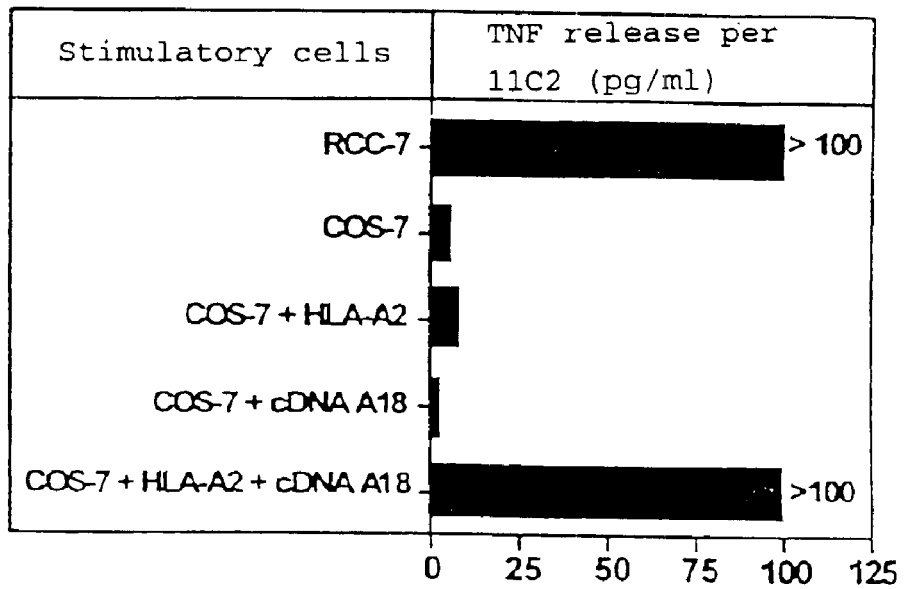

FIG. 4: Stimulation of the 11C2 CTL by the cells transiently cotransfected with the autologous HLA-A*0201 cDDN and the A18 cDNA.

The 11C2 CTL was added 48 hours after cotransfection. The TNF contained in the supernatants was estimated 20 hours later by assaying its toxicity on WEHI-164 cells (clone 13). The stimulatory cells comprise the RCC-7 cell line as a positive control and COS-7 cells which are nontransfected or transfected with the HLA*0201 cDNA alone as a negative control.

Figure 5:
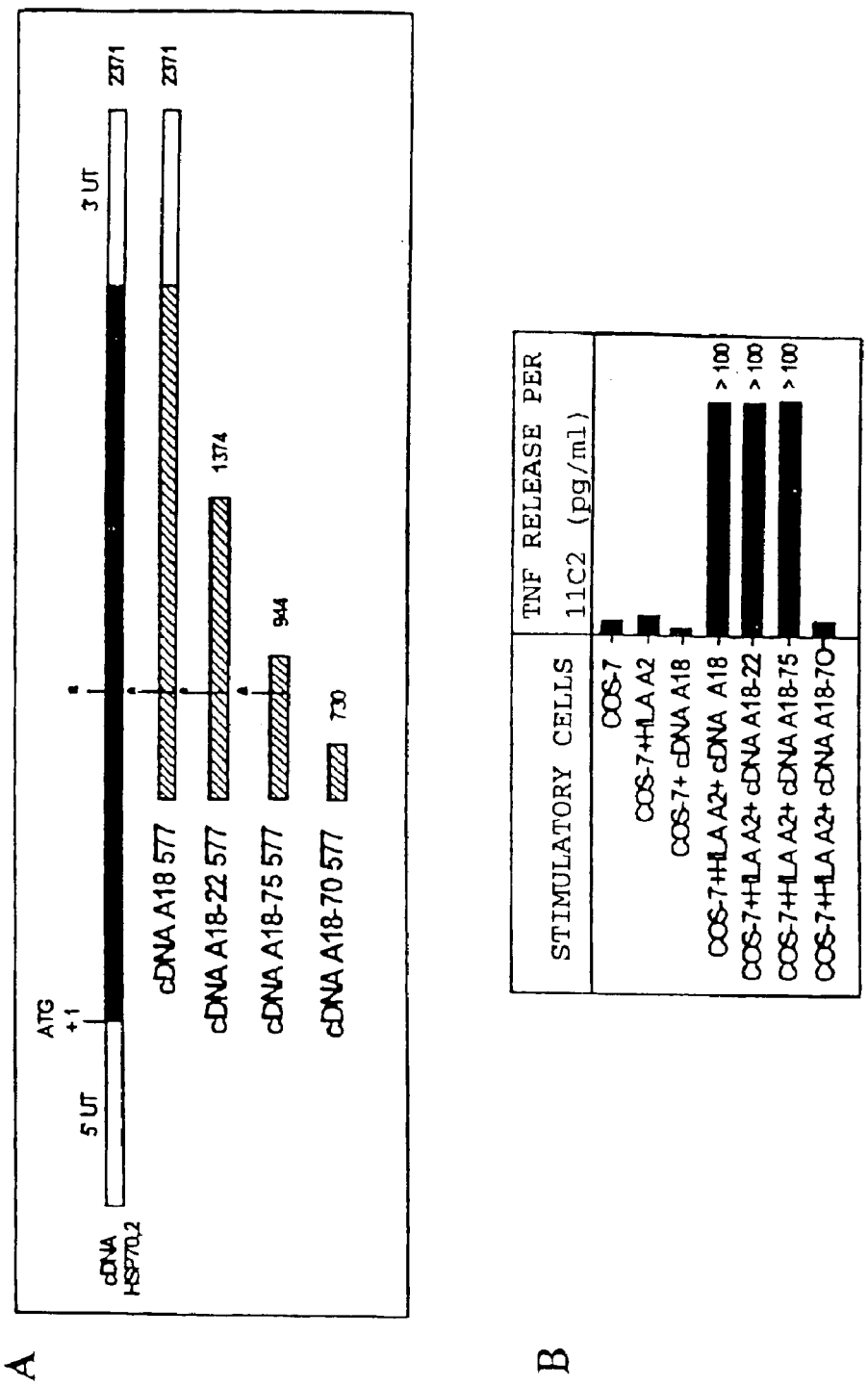

FIG. 5: Location of the epitope region of hsp70-2 recognized by the 11C2 CTL.

(A) The total length of the hsp70-2 cDNA is represented schematically in black and white. 5' UT and 3'UT correspond to the 5' and 3' untranslated regions respectively. The coding region (in black) begins with the translation start site (ATG codon) and corresponds to nucleotide+1. The multiple truncated clones obtained from the A18 cDNA are represented in gray. The A18 cDNA begins at nucleotide 577 of the coding region. The mutated nucleotide is marked with an asterisk (position 877).

(B) Illustrates the stimulation of the 11C2 CTL by COS-7 cells temporarily cotransfected with the autologous HLA-A*0201 cDNA and with each of the various truncated A18 cDNAs. The transfected cells were incubated for 24 hours with 5000 11C2 CTLs, and the LD amount of TNF was measured 20 hours later. The control stimulatory cells comprise COS-7 cells which are non-transfected or transfected with the A18 cDNA alone, as a negative control, and cotransfected with the A18 and A*0201 cDNAs as a positive control.

Figure 6:
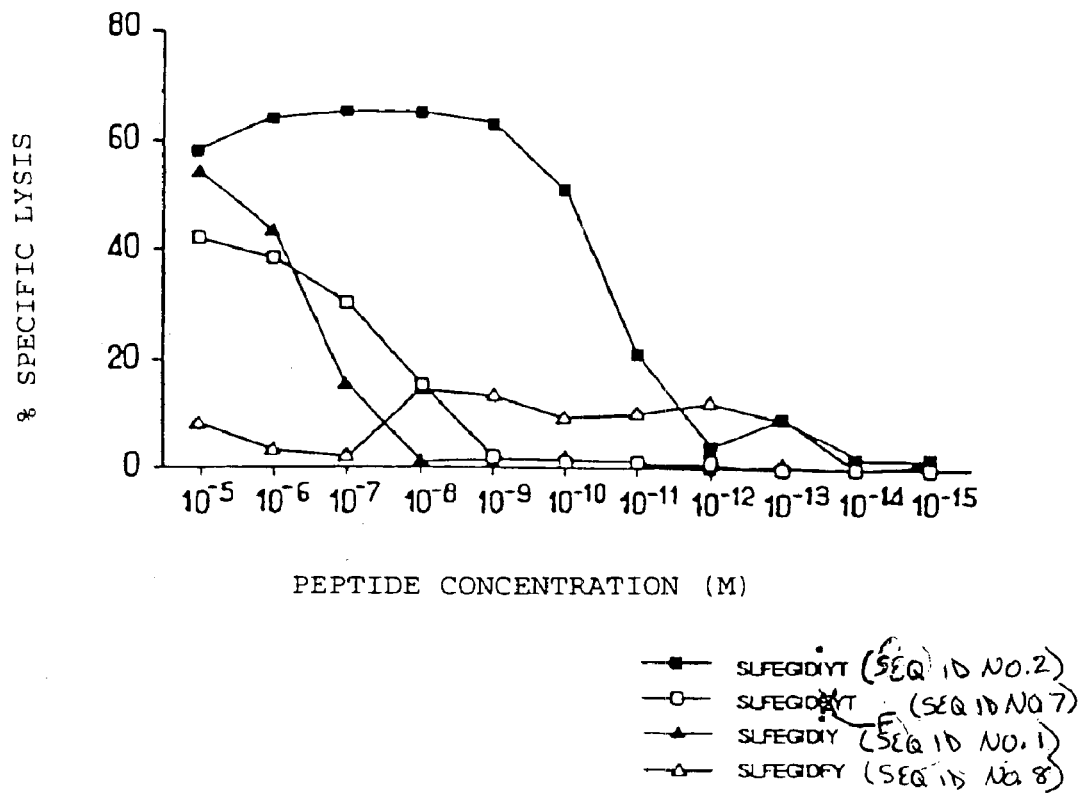

FIG. 6: Lysis by 11C2 CTLs of the autologous cell line transformed with EBV and incubated with the peptides encoded by hsp70-2

2000 cells transformed with EBV and labeled with $^{51}$Cr were incubated for 1 hour in the presence of the indicated hsp70-2 peptides (SEQ ID NOS. 2, 7, 1, and 8) at multiple concentrations. The 11C2 CTL was then added at an effector/target ratio (E/T) of 31/1. Chromium release was measured 4 hours later. The asterisks indicate the mutated amino acids.

Figure 7:
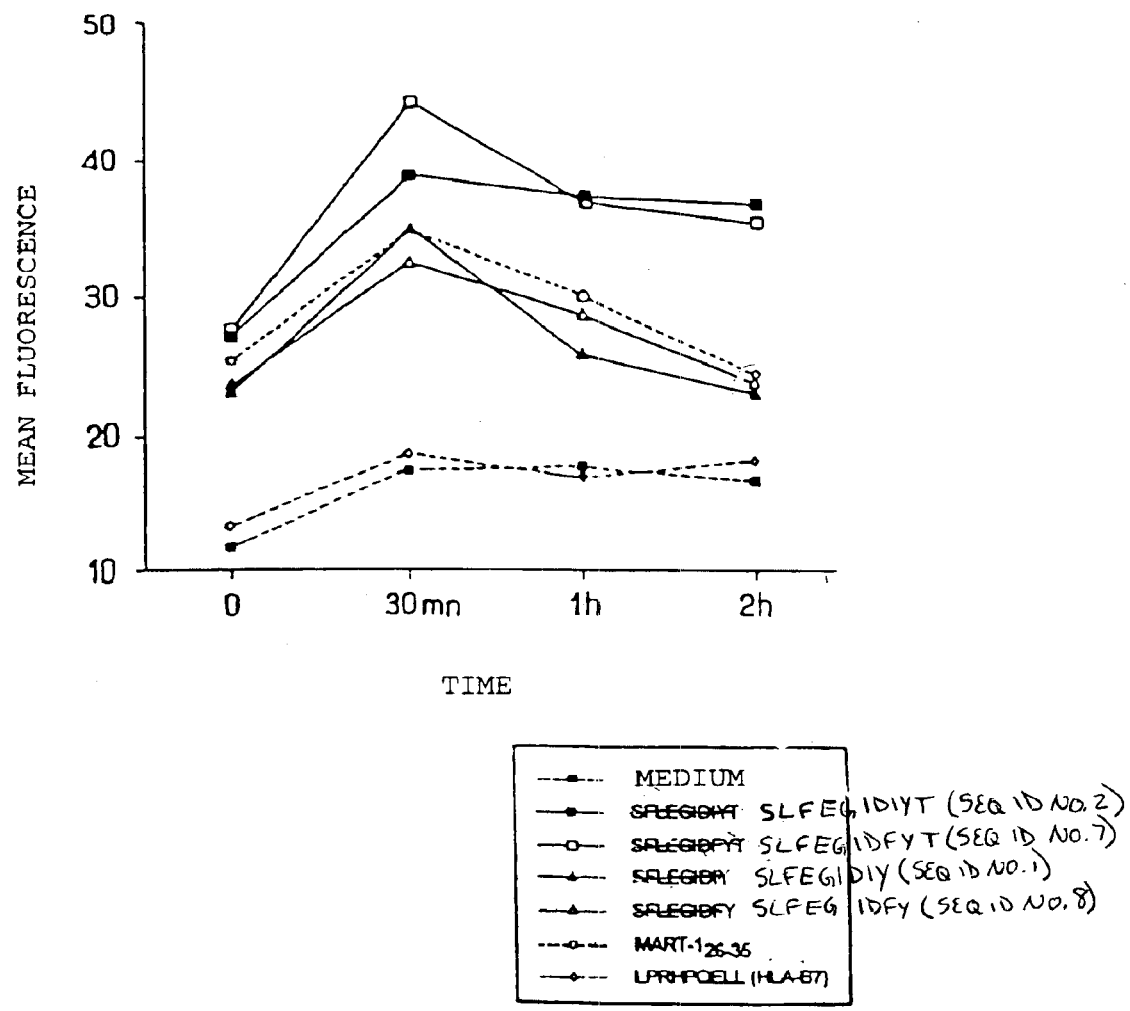

FIG. 7: Induction of HLA-A2 expression on T2 cells by the hsp70-2 antigenic peptides.

T2 cells were incubated at 26° C. for 16 hours in serum-free medium, with or without peptide at a concentration of 20 μm. Next, the peptides (SEQ ID NOS. 2, 7, 1, and 8) were again added, and the cells were incubated at 37° C. At 30-minute or one-hour intervals, the cell pellets were collected and the change in HLA-A2 expression was analyzed by flow cytometry with an anti-HLA-A2 mAb (MA2.1). The amino acid sequences of the peptides are represented. The mutated amino acid is represented by an asterisk.

Figure 8:
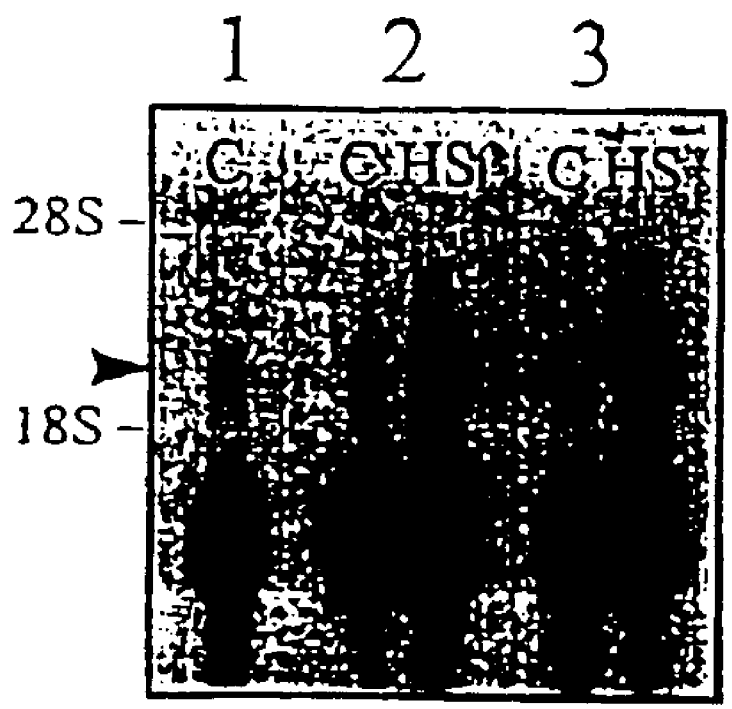

FIG. 8: Northern Blot Analysis

The total cytoplasmic RNA (15 μg), derived from the RCC-7 tumor (row No. 1), from the RCC-7 cell line (No. 2), and the autologous cell line transformed with EBV (No. 3), is maintained at 37° C. (subrow C) or treated by heat shock for 2 hours at 40° C. (subrow HS), was fractionated on denaturing formaldehyde/agarose gel and transferred onto Hybond-N$^+$ nylon membrane. The Northern Blot was hybridized with the probes consisting of a fragment specific for hsp70 and for the glyceraldehyde-3-phosphate dehydrogenase (GAPDH) cDNA. The migration position of the 28s and 18s RNAs is given. The approximately 2.4-Kb hsp70-2 transcript is indicated by an arrow above the 18s RNA and above the GAPDH mRNA.

Figure 9:
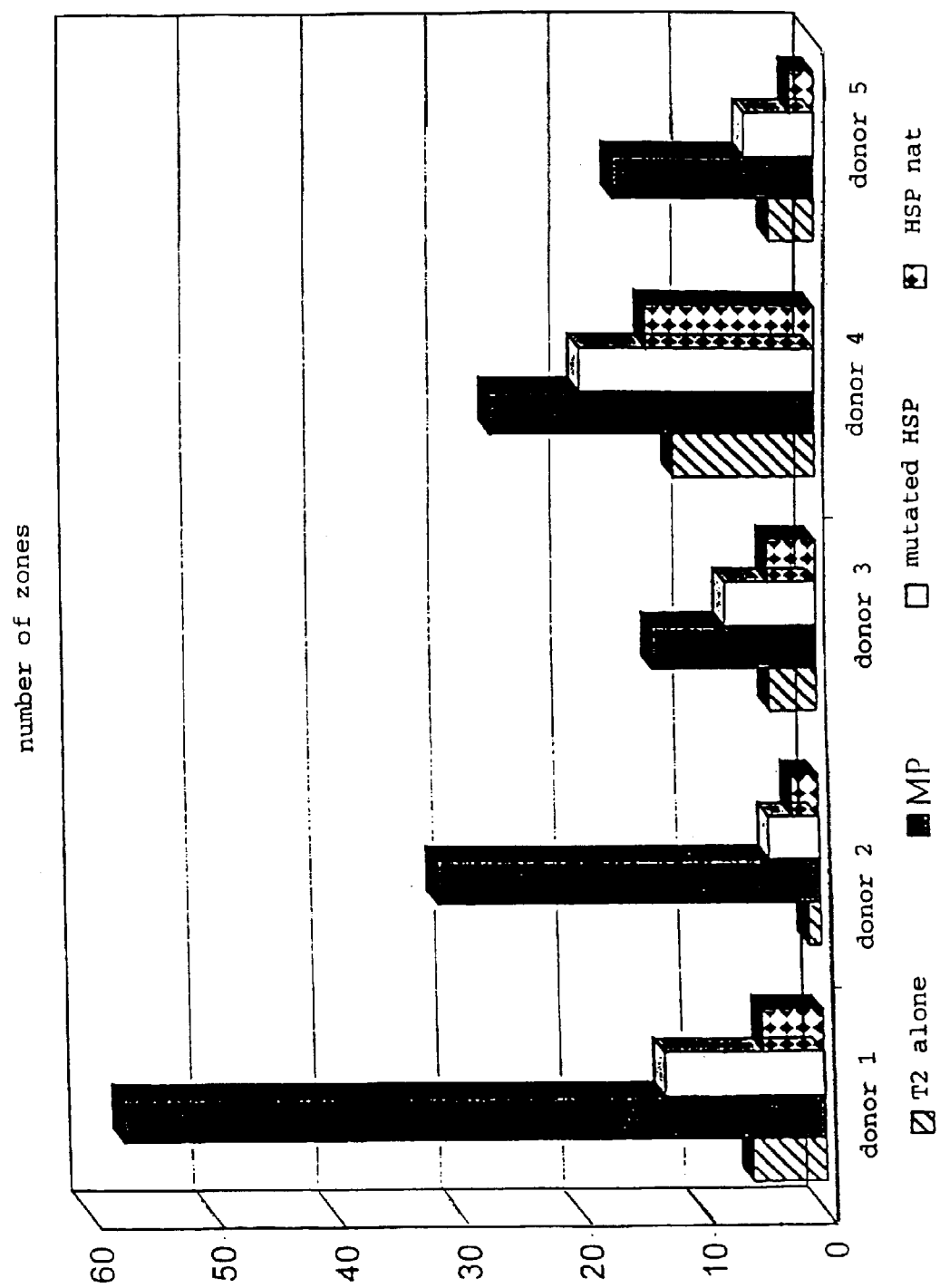

FIG. 9: Elispot assay

This figure shows that the mutation or modification brings about a highly increased immunogenecity power. Mutated hsp is the peptide compound according to the invention, hsp nat is the corresponding natural peptide (nonmutated), MP is the positive control (very immunogenic peptide of the "matrix protein" and T2 is the negative control (cells not stimulated by the peptide).

The studies of the present invention have allowed the isolation of RCC-CTL clones originating from TILs (tumor-infiltrating lymphocytes) obtained in three different experiments and using two experimental conditions (use of IL-2 or of IL-2+IL-7+IL-12). Between the 20th and 30th day, these cells, belonging to the cultures which show considerable lysis of the autologous cell line of the RCC-7 tumor, were cloned by a limiting dilution. Out of 8 clones obtained by this protocol, 5 were selected as a function of their distinct TCR phenotype. All the clones are TCR $\alpha/\beta^+$ CD8$^+$ CD4$^-$ cytotoxic cells, and produce TNF when they are stimulated by autologous cells of the tumor. The blocking effect of the anti-class 1 mAb WC/32 showed that the cytotoxic activity is MHC I molecule-restricted (FIG. 1). The lytic activity of clone 11C2 was blocked by mAb MA2.1 specific for HLA-A2 (FIG. 2). This result suggests that HLA-A2 is the presentation molecule for 11C2, and that 11C2 recognizes the autologous cells of the tumors (FIG. 3).

Identification of the cDNA of the Antigen Recognized by 11C2 CTLs

In order to identify the gene encoding the antigen a genetic approach was used, comprising the transfection of a cDNA library originating from the RCC tumor into COS-7 cells with the cDNA encoding the HLA-A2 presentation molecule, Seed B. (1987). The expression vector used contains the SV40 origin of replication, which allows a considerable multiplication of the episomes of the transfected plasmid, and thus high expression of the transfected genes. A cDNA library was used which was constructed in the pcDNA I expression vector using the RNAs originating from the RCC-7 cell line. This library was divided into 400 parts of 200 recombinant plasmids, and each part was cotransfected in duplicate with the pcDNA I autologous HLA-A*0201 construct, into COS-7 cells. The COS-7 cells were then assayed for their capacity to stimulate the production of TNF by clone 11C2. 48 hours later, the cotransfected COS-7 cells were incubated overnight with 11C2, and the TNF concentration in the supernatant was determined through its cytotoxic action on WEHI cells. The amount of TNF in the supernatants is below 5 pg/ml, except for two pairs (40 and 45 pg/ml) of duplicated experiments. The second screening was carried out by transfecting the COS cells with 100 parts of 20 recombinant plasmids originating from the extraction of double positives. Finally, a third screening led to two cDNA clones (termed A8 and B65) being isolated, which make it possible to transfer the antigen expression into the HLA-A 0201 COS-7 cells. The results obtained with the A18 cDNA clone is presented in FIG. 4.

The sequence of the longest cDNA (A18) is 1.9 Kb with 100% homology to the nucleotides from 577 to 2876 of the hsp70-2 cDNA, except for a mutation at position 877 (an adenine in place of a thymine). Position +1 is the translation start site of hsp70-2, Milner et al, 1990.

With the aim of identifying the entire length of the hsp70-2 cDNA, and in order to verify whether the mutation is only present at the tumor site, we performed a PCR (hsp70-2 is an intron-lacking gene) on the DNA originating from the extraction of RCC-7 cells and of B cells transformed with EBV and of PHA blasts. A single 2-Kb product, corresponding to nucleotide −36 to 1974, was obtained in each of the cases, and was subcloned into the vector pcDNA I for sequencing and expression. 4 of the 7 DNA clones, obtained from the tumor fragment, have the mutation. For the cells transformed with EBV and the blasts, none of the 14 DNA sequences analyzed carries the mutation. Thus, the mutation is present only on a chromosome in the tumor cells and is absent in the normal cells.

Identification of the Antigenic Peptide

In order to delimit the minimum nucleotide region encoding the antigenic peptide, multiple truncated cDNAs were obtained from the A18 cDNA clone. The use of exonuclease III made it possible to gradually generate deletions starting from the 3' end of the cDNA (FIG. 5). These cDNA fragments were cotransfected into COS-7 cells with the autologous HLA-A*0201 cDNA. A minimum coding nucleotide region was located between nucleotides 730 and 944. The truncation in the region carrying the single mutation specific for the tumor abolishes recognition by 11 C2 CTLs. Peptides carrying the HLAS-A*0201 binding motif were sought in this region, and among the 18 peptides assayed, only 2 (the nonapeptide SLFEGIDIY (SEQ ID NO: 1), amino acids 286 to 294, and the decapeptide SLFEGIDIYT (SEQ ID NO: 2), amino acids carrying the mutant isoleucine residue at position 8 were recognized. Maximum half-lysis was obtained with only $5\times10^{-11}$ M of the decapeptide, compared to $5\times10^{-7}$ M of the nonapeptide (FIG. 6). 11 C2 CTL also recognizes the wild-type decapeptide 286–295 (SLFEGIDFYT) (SEQ ID NO: 7), with a maximum half-lysis of $5\times10^{-8}$ M, but not the wild-type nonapeptide 286–294 (FIG. 6).

Binding of the hsp70-2 Peptide Fragments to HLA-A2

Antigenic peptides which can bind HLA-A2 can regulate positively the expression of HLA-A2 molecules in T2 cells, Nijman et al. (1993). The binding capacity of the hsp70-2 286-295 decapeptides (mutated and wild-type) was compared to that of the nonapeptide 286–294. The binding of these two decapeptides is stable over a period of 4 hours at 20 µM without showing any difference between the mutant and wild-type forms (FIG. 7). The hsp70-2 nonapeptides are less effective, but their binding is comparable to that of the MART-1$_{27-35}$ peptide to HLA-A2. As could be expected, no effect was observed for the control peptide HLA-B7 (see FIG. 7).

Northern Blot Analysis

A probe specific for the hsp70-2 locus, including the 3' untranslated region, was used to examine the expression of the hsp70-2 gene. A 2.4-Kb mRNA was detected in the autologous cells transformed with EBV. Similarly, a low level of expression was observed in the untreated RCC-7 cells and in the frozen surgical samples of RCC-7 (FIG. 8). Low levels of expression were also observed in other tumors, in particular in melanomas, neuroblastomas, adenocarcinomas of the colon and bladder tumor fragments.

EXAMPLE 1

Establishing RCC Cell Lines

The cell lines were established from the cells of renal carcinoma RCC, as described previously by Angevin et al, 1997. In summary, the primary tumors were obtained from untreated patients who had undergone a radical nephrectomy in our institution. Patient 7 (HLA-A2, -A29, -B44, -B51, -Cw15, -Cw16) is a 54-year-old male individual with a metastatic RCC. After surgery and enzymatic digestion, fresh cell suspensions from the RCC tumors were seeded in a culture medium composed of Dulbeccos' Modified Eagle Medium (DMEM), penicillin (50 IU/ml), streptomycin (50 µg/ml), 1% of 200 mM L-glutamine, 1% of 200 mM sodium pyruvate, 10% of fetal calf serum (FCS) and 1% of Ultroser G (Gibco-BRL, Paisley, UK). This medium is termed, in the remainder of the document, "RCC medium". All the tumor cell lines were maintained in this RCC medium. The RCC-7 cell line was obtained from the primary tumor of patient 7.

EXAMPLE 2

Cells and Culture Media

The EBV autologous cell line was obtained after infection of PBMCs of patient 7.

The cell line transformed with EBV was maintained in RPMI 1640 (Gibco-BRL), supplemented with 10% of FCS. WEHI-164 clone 13, a TNF-sensitive mouse fibrosarcoma cell line, was diligently provided by Benoit Van Den Eynde (Ludwig Institute for Cancer Research, Brussels, Belgium), and was cultured in RPMI 1640 (Seromed, Biochrom KG, Berlin, Germany) supplemented with L-glutamine, sodium pyruvate, antibiotics and 5% of FCS, at a concentration of 0.01 to $0.05 \times 10^6$ cells/ml. The mutant human cell line CEM×721.174.T2 (T2), Salter et al, (1989), was maintained in RPMI-1640 supplemented with 10% of FCS. This cell line was diligently provided by Pierre Langlade (Pasteur Institute, Paris, France). All cell cultures were maintained in an atmosphere saturated with water and with a 5% $CO_2$ content.

EXAMPLE 3

Establishing the TIL Cell Lines

The TILs, originating from the tumor suspensions, were inoculated in flasks containing RPMI 1640, penicillin, streptomycin, 1% of L-glutamine, 1% of sodium pyruvate and 8% of human AB serum (Institut Jacques Boy S.A., Reims, France), termed complete medium. The TILs were seeded at the same concentration in complete medium supplemented with 10 IU/ml of rIL-2, 50 IU/ml of rIL-7 (Sanofi, Toulouse, France) and 10 IU/ml of rIL-12 (Genetics Institute, Cambridge, Mass.), for three days. From the $3^{rd}$ day onward, the TILs were fed using the complete medium with 30 IU/ml of rIL-2, 50 IU/ml of rIL-7 and 10 IU/ml of rIL-12. The phenotype and the cytotoxic activity of the TIL cell lines were characterized after 14 and 21 days of stimulation.

EXAMPLE 4

Monoclonal Antibodies (mAbs), Serological Agent and Phenotypic Analysis

The mAbs conjugated either to fluorescein (FITC) or to phycoerythrin (PE), and directed against the TCR α/β, CD3 (Leu4), CD4 (Leu3a), CD8 (Leu8), CD80 (B7.1) and HLA DR (L249), were purchased from Becton Dickinson (Mountain View, Calif.). CD56 (NKH1A) originates from Coultronics (Hialeah, Fla.). The TILs were characterized by double immunostaining, by incubating the cells for 30 min at 4° C. with FITC- or PE-mAb. The flow cytometry analysis was carried out on a FACScan (Becton Dickinson) and using the Cellquest software. The laboratory ascites were W6.32 (anti-HLA-A/B/C), MA2.1 (anti-HLA-A2 and -B17) and B1.23.2 (anti-HLA-B/C), and were selected for the functional and immunofluorescence experiments, at predetermined saturation concentrations up to a final dilution of between 1/200 and 1/2000.

EXAMPLE 5

Cloning of the TIL Cell Lines

After culturing for 3 weeks, the lymphocytes were cloned by diluting them to the limit. The cloning was performed between 600 and 0.6 cells/well, in 96-well plates containing RPMI medium supplemented with 8% of human AB serum, 30 IU/mL of rIL-2 and 3% of TCGF. At the bottom of the wells, a feeder layer was cultured consisting of irradiated autologous tumor cells ($1 \times 10^4$/well), of irradiated allogenic lymphocytes ($8 \times 10^4$ per well) and of irradiated cells transformed with EBV ($2 \times 10^4$/well). The clones were fed three times per week with the complete medium containing rIL2 and TCGF. The immunological phenotype and the cytotoxicity were characterized for the cloned cells.

EXAMPLE 6

Cytotoxicity Assay

The cytotoxicity assays were carried out using the standard 4-hour chromium release assay, as described above, Angevin et al, (1997). In summary, $2 \times 10^3$ $^{51}$Cr-labeled target cells were incubated for 4 hours at 37° C., with the effector cells at various E/T ratios, in a final volume of 200 µl. With regard to lysis inhibition by the mAbs, the target cells were preincubated for two hours in the presence of saturating concentrations of mAb, before adding the effector cells. At the end of the incubation, 40 µl of supernatant were transferred to Lumaplate 96 solid scintillation plates (Packard Instruments, Meriden, Conn.), were dried overnight and counted in a beta-radioactivity counter (Packard Instruments).

EXAMPLE 7

Cloning and Expression of the HLA Molecules

The class 1 HLA alleles were cloned using the PCR method described by Ennis et al, (1990), with a few slight modifications. The total RNA was prepared from the RCC-7 cell line using $RNA^B$ (Bioprobe Systems). The C) first cDNA strand was synthesized with an oligo(dT) probe and reverse transcriptase (Invitrogen). The cDNA was used as a matrix for a 30-cycle PCR amplification with the following probes:

5P2-H (5'-GGGCAAGCTTGGACTCAGAATCTCCCCAGACGCCGAG-3'), SEQ ID No. 3-

3P2-X (5'-GCCCTCTAGATCTCAGTCCCTCACAAGGCAGCTGTC-3'), SEQ ID No. 4

These probes correspond to the consensus sequences of the 5' and 3' untranslated regions, respectively, of the class 1 alleles. These probes are identical to the HLA-5P2 and HLA-3P2 probes described above, Ennis et al. (1990), except for the cloning site (the Sal I and Hind III sites for 5P2, and the Hind III and Xba I sites for 3P2, respectively, were replaced. The PCR products were digested with Hind III and Xba I, and ligated into the plasmid pcDNA I (Invitrogen) These constructs were transfected into E. coli MC 1061/P3. The plasmid DNA was then extracted from several colonies using QIAGEN columns (Qiagen). The DNA sequencing was carried out using the "ABI PRISM Dye Terminator cycle sequencing ready reaction kit" (Applied Biosystems) and an automatic DNA sequencer. The sequences were compared to the class I HLA nucleotide sequences available in the databases.

EXAMPLE 8

Construction of the cDNA Library

The poly(A)+ RNA was extracted from the RCC-7 cell line using the mRNA isolation system (Fast Track kit 2.0, Invitrogen), respecting the manufacturer's instructions. The first cDNA strand was synthesized using AMV reverse transcriptase with an oligo-dT probe containing a Not I site at its 5' end. The RNA-cDNA hybrid created by the synthesis of the first strand was transformed into double-stranded cDNA with DNA polymerase I in combination with Rnase H and DNA ligase from E. coli. Next, T4 DNA polymerase was used to produce a blunt cleavage in the cDNA. BstX I linkers were added, and the size of the cDNA was obtained by fractionation on agarose gel. The cDNA of desired size (longer than 800 nucleotides) was ligated into the vector pcDNA I cleaved with BstX I/Not I, and the suitable E. coli strain (MC1061/P3) was transformed. For the screening experiments, the plasmid DNA obtained from some bacterial colonies was prepared according to the following protocol: 100 or 200 colonies, cultured in LB-agar medium (with 30 $\mu$l/ml of ampicillin and 10 $\mu$l/ml of tetracycline, were seeded in 2 ml of LB medium and incubated overnight at 37° C. The plasmid DNA was extracted using the alkaline lysis method, Birnboim et al, (1979), and was resuspended in 30 $\mu$l in 10 mM Tris-1 mM EDTA, pH 7.5, containing 20 $\mu$l/ml of RNAse A. The plasmid DNA concentration was adjusted to 40 ng/$\mu$l.

EXAMPLE 9

Transfection of COS-7 Cells and Screening of Transfectants

The transfection experiments were carried out by the "DEAE-dextran-chloroquin method, Brichard et al, (1993). Three days before transfection, the COS-7 cells were seeded in 96-microwell plates at the concentration of $5 \times 10^3$ cells/well, in 150 $\mu$l of RPMI medium containing 20% of fetal calf serum. For the transfection, the medium was replaced with 30 $\mu$l of DEAE-Dextran/DNA mixture. These mixtures were prepared for double transfections in microwells by adding sequentially:

200 ng of plasmid DNA originating from the cDNA library, 200 ng of plasmid pcDNA I/HLA-A*0201, 25 $\mu$l of 150 mM NaCl, 10 mM Tris, pH 7.4 (termed TBS buffer), 35 $\mu$l of TBS containing 1 mg/ml of DEAE-Dextran (Pharmacia Biotech Europe GmbH, Saclay, France).

The cells were incubated with this mixture plus 105 $\mu$l of DMEM supplemented with 10% of non-complemented "NuSerum" (Becton Dickinson) and 100 mM of chloroquin (Sigma-Aldrich Chimie SARL, Saint Quentin Fallavier, France), for 30 minutes at room temperature. Next, the cells were incubated for 4 hours at 37° C. under a 5% $CO_2$ atmosphere. After incubation, the medium was removed, and the cells were incubated for 2 min in 1×PBS containing 10% of a solution of dimethyl sulfoxide. The cells were washed once with 1×PBS, and incubated in RPMI containing 10% of FCS for 48 hours. The medium was then removed and the cells were washed once with 1×PBS. 5000 CTLs were added to the wells in 100 $\mu$l of RPMI containing 10% of FCS, After 20 hours, the supernatant was collected and its TNF content was determined by assaying its cytotoxicity on WEHI-164 clones 13 in an MTT(3-[4,5-dimethylthiozole]-2,5-diphenyltetrazolium bromide (Sigma-Aldrich) calorimetric assay, as described previously, Traversari et al, (1992). With regard to the inhibition of the secretion of TNF by the mAbs, the target cells were preincubated for 2 hours in the presence of a saturating concentration of mAbs, before adding the effector cells for a further 20 hours.

EXAMPLE 10

PCR Assay for Isolating the Entire Length of hsp70-2

The genomic DNA was extracted from the RCC-7 cell line with DNAzol™ (Life Technologies). 1 $\mu$l of DNA was used for a PCR reaction using Taq DNA polymerase (Perkin Elmer). The following probes were used:

the hsp70-2A probe, 5'-GGGCAAGCTTAGTCT-CAGAGCGGAGCCAAC-3'

(nucleotides -36 to -18, sense), SEQ ID No. 5, the hsp70-2B probe, 5'-GCCCTCTAGAGTCCCAACA-GTCCACCTCAA-3'

(nucleotides 1955 to 1974, antisense), SEQ ID No. 6. These probes contain the Hind III and Xba I restriction sites, respectively. The conditions for the PCR were 98° C. for 1 min, followed by 30 amplification cycles (98° C. for 15 sec, 65° C. for 1 min, 72° C. for 2 min, with a final extension for 10 min at 72° C.). The PCR product obtained was digested with Hind III and Xba I and purified on absorbent glass beads (Geneclean), and was then subcloned into the Hind III and Xba I sites of the expression vector pcDNA I for sequencing and cotransfection, with HLA-A*0201, into the COS-7 cells.

EXAMPLE 11

Identification of the Minimum Nucleotide Coding Region for the Antigenic Peptide The A18 cDNA was isolated from the cDNA library manufactured from the expression vector pcDNA I. The plasmid was digested with Sph I and Xba I, before treatment with exonuclease III in order to generate gradual deletions starting from the 3' end of the A18 cDNA. In order to obtain a considerable number of truncated cDNA clones, the "Exo Mung Bean Deletion Kit" (Stratagene) was used. After ligation, the bacterium E. coli MC1061/P3 was transformed with the truncated cDNAs. The plasmid DNA was extracted from each clone, and then sequenced and cotransfected, with HLA-A*0201 into the COS-7 cells.

EXAMPLE 12

Peptide Synthesis and Peptide Recognition Assay

In the screening assay, the peptides used were synthesized by "PepSet technology" (Chiron Technologies, Suresnes, France). For the functional assays, the peptides were synthesized on solid phase using F-moc (temporary NH2-terminal protection), and were purified by preparative HPLC. The analytical HPLC indicates that the peptides are at least 95% pure. The lyophilized peptides were dissolved in 10 mM of DMSO in water, and conserved at -20° C. The peptides were used in a chromium release assay. 2000 autologous cells transformed with EBV, and labeled with $^{51}$Cr, were incubated for 1 hour at 37° C. on 96-well plates, with diverse concentrations of peptides, before adding 11C2 CTLs.

EXAMPLE 13

Peptide Binding Assay

T2 cells, Nijman et al, (1993), were cultured 48 hours before the assay, in a serum-free AIM-VWmedium (Gibco-BRL). For the binding assays, the T2 cells (106) were incubated at 26° C. for 16 hours in the same medium in 0.8% of DMSO, with or without peptide at a concentration of 20

μM. Next, the peptides (20 μM) were again added, and the cells were incubated at 37° C. At 30-min or one-hour intervals, the cell pellets were collected, and the HLA-A2 expression level was monitored using the anti-HLA-A2 mAb (MA2.1).

EXAMPLE 14

RN Isolation and Northern Blot Analysis

The cells were either maintained at 37° C. or underwent a heat shock at 42° C. for 2 hours, before recovery by centrifugation. The total RNA was extracted by guanidinium isothocyanate lysis, and was ultra-centrifuged in cesium chloride. Samples of total RNA (15 μg) were fractionated in a denaturing gel containing 1% of formaldehyde-agarose, and were transferred onto Hybond-N+nylon membranes respecting the manufacturer's instructions (Amersham France S.A., les Ulis, France). The Northern Blot was hybridized with a probe specific for hsp70-2 (nucleotides 1955 to 2159) and with the glyceraldehyde-3-phosphate dehydrogenase (GAPDH) probe. All probes were labeled with [$^{32}$P] dCTP (3000 Ci mmol$^{-1}$) using the Prime-IT™ II Random Primer labeling Kit (Stratagene). The hybridization was carried out at 45° C. for 16 hours with the hsp70-2 probe (106 cpm/ml) and the GAPDH probe (105 cpm/ml). The membranes were washed twice with 2×SSC at room temperature, once for 45 min with 2×SSC/0.1% SDS at 62° C., and once at 62° C. for 10 min with 0.1×SSC, before autoradiography at 80° C. for 11 days.

EXAMPLE 15

Elispot Assay

CD8+cells were isolated from HLA-A2-positive donors by negative immunomagnetic purification (using antibodies against CD4 and CD56 cells). 100,000 CD8+cells were directly added to 100,000 HLA-A2.1-positive T2 cells loaded with 10$^{-6}$ M of peptides, in 96-well plates in which the bottom is coated with nitrocellulose (Millipore). After stimulation of the CD8+ cells for 20 hours, an Elispot-IFNγ assay was performed. The results are given in Table I below. The positive control is the peptide MP or "matrix protein", this being an influenza virus envelope protein which is very immunogenic in humans.

TABLE I

Elispot-IFNγ assay results

|  | Donor 1 | Donor 2 | Donor 3 | Donor 4 | Donor 5 |
|---|---|---|---|---|---|
| T2 alone | 6 | 1 | 3.833 | 11.5 | 3.75 |
| MP | 57.25 | 31.33 | 13.33 | 26.5 | 16.5 |
| mutated hsp | 13 | 4.167 | 7.5 | 19.25 | 5.75 |
| hsp nat | 5 | 2.167 | 4 | 13.75 | 2 |

These results show that it is possible to induce human CD8 lymphocytes from healthy HLA-A2+individuals with the preferred peptide compound of the invention (SEQ ID No. 1 and 2), but not with the corresponding nonmutated peptide. It clearly emerges that the mutation brings about a highly increased immunogenicity power, since lymphocytes which have never been stimulated by this peptide are able to secrete interferon gamma within 24 hours, without any culturing in vitro or addition of cytokines.

REFERENCES

Alexander J. P., Kudoh S., Melsop K. A., Hamilton T. A., Edinger M. G., Tubbs R. R., Sica D., Tuason L., Klein E., Bukowski R. M., and Finke J. H. 1993, T-cells infiltrating renal cell carcinoma display a poor proliferative response even though they can produce interleukin 2 and express interleukin 2 receptors. Cancer Res. 53: 1380.

Angevin E., Kremer F., Gaudin C., Hercend T., and Triebel F. 1997, Analysis of T-cell immune response in renal cell carcinoma; polarization to type 1-like differentiation pattren, clonal T cell expansion and tumor-specific cytotoxity, Int. J. Cancer 72: 431.

Bernhard H., Karbach J., Wolfel T., Busch P., Storkel S., Stockle M., Wolfel C., Seliger B., Huber C., Buschenfelde K. H. M. z., and Knuth A. 1994, Cellular immune response to human renal-cell carcinomas; definition of a common antigen recognized by HLA-A2 restricted cytotoxic T-lymphocyte (CTL) clones. International Journal of Cancer 59: 837.

Birnboim H. C., and Doly J. 1979. A rapid alkaline extraction procedure for screening recombinant plasmid DNA. Nucleic Acid, Res. 7:1513. Blachere N. E., Li Z., Chandawarkar R. Y., Suto R., Jaikaria N. S., Basu S., Udono H., and Srivastava P. K.

1997. Heat shock protein-peptide complexes, reconstituted in vitro, elicit peptide-specific cytotoxic T lymphocytes response and tumor immunity. J. Exp. Med. 186: 1315.

Brichard V., Pel A. V., Wölfel T., Wölfel C., Plaen E. D., Lethé B., Coulie P., and Boon T. 1993. The tyrosinase gene codes for an antigen recognized by autologous cytolytic T lymphocytes on HLA-A2 melanomas. J. Exp. Med. 178: 489.

Brouwenstijn N., Gaugler B., Kruse K. M., Spek C. W. V. d., Mulder A., Osanto S., Eynde B. J. V. d., and Schrier P. I. 1996. Renal-cell carcinoma-specific lysis by cytotoxic T-lymphocyte clones isolated from peripheral blood lymphocytes and tumor-infiltrating lymphocytes. Inter. J. Cancer 68: 177.

Ennis P. D., Zemmour J., Salter R. D., and Parham P. 1990. Rapid cloning of HLA-A,B cDNA by using the polymerase chain reaction: Frequency and nature of errors produced in amplification. Proc. Natl. Acad. Sci. 87: 2833.

Even J., Lim A., Puisieux I., Ferradini L., Dietrich P. Y., Toubert A., Hercend T., Triebel F., Pannetier C., and Kourilsky P. 1995. T-cell repertoires in healthy and diseased human tissues analysed by T-cell receptor beta-chain CDR3 size determination: evidence for oligoclonal expansions in tumours and inflammatory diseases. Research Immunology. 146: 65.

Farace F., Angevin E., Poullion I., Leboullaire C., Ferir G., Elias D., Escudier B., and Triebel F. 1997. T-cell receptor CDR3 size distribution analysis to evaluate specific T-cell response to cancer vaccines. Inter. J. Cancer 71: 972.

Finke J. H., Zea A. H., Stanley J., Longo D. L., Mizoguchi H., Tubbs R. R., Wiltrout R. H., O'Shea J. J., Kudoh S., Klein E., Bukowski R. M., and Ochoa A. C. 1993. Loss of T-cell receptor zeta chain and p56lck in T-cells infiltrating human renal cell carcinoma. Cancer Research, 53: 5613.

Gaugler B., Brouwenstijn N., Vantomme V., Szikora J. P., Spek C. W. V. d., Patard J. J., Boon T., Schrier P., and Eynde B. J. V. d. 1996. A new gene coding for an antigen recognized by autologous cytolytic T lymphocytes on a human renal carcinoma. Immunogenetics. 44: 323.

Genevee C., Diu A., Nierat J., Caignard A., Dietrich P. Y., Ferradini L., Roman-Roman S., Triebel F., and Hercend T. 1992. An experimentally validated panel of subsfamily-specific oligonucleotide primers (Valpha1-w29/Vbetal-w24) for the study of human T cell receptor variable V gene segment usage by polymerase chain reaction. Eur. J. Immunol. 22: 1261.

Gruen J. R., and Weissman S. M. 1997. Evolving views of the major histocompatibility complex. Blood. 90: 4252.

Harris SR; Thorgeirsson UP, Tumor angiogenesis: biology and therapeutic prospects, In Vivo 1998 November–December; 12(6): 563–70

Herr W, Protzer U, Lohse A W, Gerken G, zum Buschenfelde K H M, Wolfel T. Quantification of CD8+Lymphocytes Responsive to Human Immunodeficiency Virus (HIV) Peptide Antigens in HIV-Infected Patients and Seronegative Persons at High Risk for Recent HIV Exposure. Journal of InfDis 1998; 178: 260–265.

Herr W, Schneider J, Lohse A W, zum Buschenfelde K H M, Wolfel T. Detection and quantification of blood derived CD8+T lymphocytes secreting tumor necrosis factor alfa in response to HLA-A2.1 binding melanomy and viral peptide antigens. Journal of 1 mm Meth 191; 1996; 131–142.

Herr W, Linn B, Leister N, Wandel E, Meyer zum Buschenfelde K H, Wolfel T. The use of computer-assisted video image analysis for the quantification of CD8+T lymphocytes producing tumor necrosis factor spots in response to peptide antigens. Journal of 1 mm Meth 1997; 203: 141–152.

Kumar A., Farace F., Gaudin C., and Triebel F. 1996. Clonal T cell expansion induced by interleukin-2 therapy in blood and tumors. J. Clin. Invest. 97: 1219.

Locopo N; Fanelli M; Gasparini G. Clinical significance of angiogenic factors in breast cancer, Breast Cancer Res Treat 1998; 52(1–3): 159–73., Maier J A; Morelli D; Lazzerini D; Menard S.; Colnaghi M I; Balsari A, Inhibition of fibronectin activated migration of microvascular endothelial cells by IL1 alpha, TNF alpha and IF gamma, Cytokine 1999 February; 11(2): 134–9. Milner C. M., and Campbell R. D., 1990. Structure and expression of the three MHC-linked hsp70 genes. Immunogenetics. 32:242.

Milner C. M., and Campbell R. D., 1992. Polymorphic analysis of the three MHC-linked hsp70 genes. Immunogenetics. 36:357.

Nestle F. O., Alijagic S., Gilliet M., Sun Y., Grabbe S., Dummer R., Burg G. and Schadendorf D., 1998. Vaccination of melanoma patients with peptide or tumor lysate-pulsed dendritic cells. Nature Medicine 3 328:332.

Nijman H. W., Houbiers J. G., Vierboom M. P., Burg S. H. v. d., Drijfhout J. W., D'Amaro J., Kenemans P., Melief C. J., and Kast W. M. 1993. Identification of peptide sequences that potentially trigger HLA-A2.1-restricted cytotoxic T lymphocytes. Eur. J. Immunol. 23(6): 1215.

Pannetier C., Cochet M., Darche S., Casrouge A., Zoller M., and Kourilsky P. 1993. The sizes of the CDR3 hypervariable regions of the murine T-cell receptor beta chains vary as a function of the recombined germ-like segments. Proc. Natl. Acad.Sci. USA 90:2472.

Paper DH, Natural products as angiogenesis inhibitors, Planta Med 1998 December; 64(8): 686–95.

Rosenberg S. A. 1992. The immunotherapy and gene therapy of cancer. Journal of Clinical Oncology 10: 180. Rosenberg S. A., Yang J. C., Schwartzentruber D. J., Hwu P., Marincola F. M., Topalian S. L., Restifo N. P., Dudley M. E., Schwartz S. L., Spiess P. J., Wunderlich J. R., Parkhurst M. R., Kawakami Y., Seipp C. A., Einhorn J. H. and D. E. White 1998. Immunologic and therapeutic evaluation of a synthetic peptide vaccine for the treatment of patients with metastatic melanoma. Nature Medicine 3 321:327.

Salter R. D., Norment A. M., Chen B. P., Clayberger C., Kresky A. M., Littman D. R., and Parham P. 1989. Polymorphism in the alpha3 domain of HLA-A molecules affects binding to CD8. Nature 338: 345.

Scheibenbogen C, Lee K H, Stevanovic S, Witzens M, Willhauck M, Waldmann V, Nacher H, Rammensee H G, Keilhoz U.

Analysis of the T cell response to tumor and viral peptide antigens by an IFN-gammy ELISPOT assay. Int. Journal Cancer 1997; 932–936.

Sheu JR; Fu CC; Tsai ML; Chung WJ, Effect of U-995, a potent shark cartilage-derived angiogenesis inhibitor, on anti-angiogenesis and anti-tumor activities. Anticancer Res 1998 November–December; 18(6A):4435–41.

Traversari C., Van der Bruggen P., Luescher I. F., Lurquin C., Chomez P., Van Pel A., De Plaen E., Amar-Costesec A., and Boon T, 1992. A nonapeptide encoded by human gene MAGE-1 is recognized on HLA-A1 by cytolytic T lymphocytes directed against tumor antigen MZ2-E. J. Exp. Med. 176: 1453.

Vitiello A., Ishioka G., Grey H. M., Rose R., Farness P., LaFond R., Yuan L., Chisari F., V., Furze J., Bartholomeuz R., and Chesnut R. W., 1995. Development of a lipopeptide-based therapeutic vaccine to treat chronic HBV infection. J. Clin. Invest. 95 341:349.

What is claimed is:

1. A peptide compound comprising the amino acid sequence of SLFEGIDIY (SEQ ID No: 1) or SLFEGIDIYT (SEQ ID No: 2).

2. The peptide compound as claimed in claim 1, wherein the amino acid sequence is SEQ ID No: 1.

3. The peptide compound as claimed in claim 1, further comprising at least one element selected from the group consisting of:

a protective chemical group able to protect peptides against proteases and reacting with NH2 or COOH, or with both NH2 and COOH, provided that this modification does not significantly lower the immunogenicity of the peptide, chemical groups improving the effectiveness of a peptide in vivo, lipids or fatty acids, covalently linked to the peptide fragments so as to form lipopeptides, a carrier protein possessing restriction sites and enabling intact peptide fragments to be conveyed to their sites of action in the body.

4. A composition comprising a peptide compound according claim 1 and a pharmaceutically acceptable vehicle.

5. The composition as claimed in claim 4, further comprising at least one immunological adjuvant.

6. The composition as claimed in claim 4, comprising a pharmaceutical vehicle which is compatible with IV, subcutaneous, oral or nasal administration.

7. The composition as claimed in claim 4 further comprising pharmaceutical vehicle chosen from positively charged liposomes, negatively charged liposomes, nanoparticles, and lipid emulsions.

8. A composition comprising a peptide compound according to claim 2 and a pharmaceutically acceptable vehicle.

* * * * *

SEQUENCE LISTING

```
<160> NUMBER OF SEQ ID NOS: 8

<210> SEQ ID NO 1
<211> LENGTH: 9
<212> TYPE: PRT
<213> ORGANISM: Homo sapiens

<400> SEQUENCE: 1

Ser Leu Phe Glu Gly Ile Asp Ile Tyr
 1               5

<210> SEQ ID NO 2
<211> LENGTH: 10
<212> TYPE: PRT
```

<213> ORGANISM: Homo sapiens

<400> SEQUENCE: 2

Ser Leu Phe Glu Gly Ile Asp Ile Tyr Thr
 1               5                   10

<210> SEQ ID NO 3
<211> LENGTH: 37
<212> TYPE: DNA
<213> ORGANISM: Homo sapiens

<400> SEQUENCE: 3
gggcaagctt ggactcagaa tctccccaga cgccgag             37

<210> SEQ ID NO 4
<211> LENGTH: 36
<212> TYPE: DNA
<213> ORGANISM: Homo sapiens

<400> SEQUENCE: 4
gccctctaga tctcagtccc tcacaaggca gctgtc              36

<210> SEQ ID NO 5
<211> LENGTH: 30
<212> TYPE: DNA
<213> ORGANISM: Homo sapiens
<220> FEATURE:
<223> OTHER INFORMATION: HSP702A probe

<400> SEQUENCE: 5
gggcaagctt agtctcagag cggagccaac                     30

<210> SEQ ID NO 6
<211> LENGTH: 30
<212> TYPE: DNA
<213> ORGANISM: Homo sapiens
<220> FEATURE:
<223> OTHER INFORMATION: HSP70-2B probe

<400> SEQUENCE: 6
gccctctaga gtcccaacag tccacctcaa                     30

<210> SEQ ID NO 7
<211> LENGTH: 10
<212> TYPE: PRT
<213> ORGANISM: Homo sapiens

<400> SEQUENCE: 7

Ser Leu Phe Glu Gly Ile Asp Phe Tyr Thr
 1               5                   10

<210> SEQ ID NO 8
<211> LENGTH: 9
<212> TYPE: PRT
<213> ORGANISM: Homo sapiens

<400> SEQUENCE: 8

Ser Leu Phe Glu Gly Ile Asp Phe Tyr
 1               5